United States Patent [19]

Milly

[11] 4,204,121

[45] May 20, 1980

[54] CYLINDRICAL METHOD OF QUANTIFYING FUGITIVE EMISSION RATES FROM POLLUTION SOURCES

[75] Inventor: George H. Milly, Potomac, Md.

[73] Assignee: Geomet, Incorporated, Gaithersburg, Md.

[21] Appl. No.: 1,997

[22] Filed: Jan. 8, 1979

Related U.S. Application Data

[63] Continuation-in-part of Ser. No. 895,427, Apr. 12, 1978, Pat. No. 4,135,092.

[51] Int. Cl.$^2$ .......................... G01J 1/00; G01N 31/00
[52] U.S. Cl. ..................................... 250/343; 250/345; 73/23
[58] Field of Search .............. 250/341, 343, 344, 345; 356/51, 416, 432, 438; 73/23, 28, 170 R, 170 A, 432 R

[56] References Cited

U.S. PATENT DOCUMENTS

| | | | |
|---|---|---|---|
| B 532,679 | 4/1976 | Pretet | 73/170 A |
| 2,390,739 | 12/1945 | Scherbatskoy | 73/170 R |
| 2,468,021 | 4/1949 | Black | 73/28 |
| 2,645,941 | 7/1953 | Reid | 73/170 R |
| 3,229,517 | 1/1966 | Smith | 73/170 R |
| 3,670,572 | 6/1972 | Devereux et al. | 73/170 R |
| 3,820,897 | 6/1974 | Roess | 356/301 |
| 4,056,969 | 11/1977 | Barringer | 73/28 |

Primary Examiner—Alfred E. Smith
Assistant Examiner—Janice A. Howell
Attorney, Agent, or Firm—David H. Semmes; Warren E. Olsen

[57] ABSTRACT

Cylindrical method of quantifying fugitive emission rates from pollution sources, such as those emanating from ore mines, factories, office buildings, and the like.

The method is characterized by its ability to quantify airborne fugitive emissions by defining an arcuate profile of pollutant flux, while driving a pollutant sensor in a peripheral arc surrounding the pollution source. According to wind changes, the pollutant sensor may be advanced peripherally of the pollution source to an arcuate detection plane downwind, so as to quantify fugitive emission rates, regardless of source emission characteristics or wind direction.

18 Claims, 3 Drawing Figures

PLAN VIEW

VERTICAL PROFILE OF POLLUTION FLUX OBTAINED FROM A SINGLE CROSSWIND PASS ON THE DOWNWIND SEGMENT OF ARC OF THE PERIPHERAL TRACK

CYLINDRICAL METHOD OF QUANTIFYING FUGITIVE EMISSION RATES FROM POLLUTION SOURCES

CROSS-REFERENCES TO RELATED APPLICATIONS

A continuation-in-part of applicant's earlier filed METHOD OF QUANTIFYING FUGITIVE EMISSION RATES FROM POLLUTION SOURCES (Ser. No. 895,427 filed Apr. 12, 1978), issued as U.S. Pat. No., 4,135,092. In the parent patent, a transverse pollution detection plane was defined downwind of a pollution source. In the present application, continuous monitoring of the pollution source is provided by driving a pollution sensor in a peripheral arc surrounding the pollution source, while outlining an arcuate pollution detection plane at a downwind index point. As the downwind index point is determined, the pollutant sensor is advanced peripherally thereto and reciprocated through an arcuate detection plane, encompassing the index point and estimated pollutant plane.

BACKGROUND OF THE INVENTION (1). Field of the Invention

Pollution control, particularly methods for quantification of airborne fugitive emissions.

(2). Description of the Prior Art

The prior art is of a record in the parent application, U.S. Pat. No., 135,092.

SUMMARY OF THE INVENTION

According to the present invention, fugitive emission rates are monitored within a cylindrical profile, surrounding the pollution source. For example, in the case of an ore mine, driving a pollutant sensor in a peripheral arc surrounding the mine; gauging wind velocity and direction at an index point downwind of the mine; advancing the pollutant sensor to the index point; defining an arcuate pollution detection plane, so as to encompass the index point and the estimated pollutant plume; sensing pollutant concentration at a series of height intervals within the vertical and lateral confines of the arcuate pollution detection plane, so as to obtain integrated products of crosswind concentration of wind speed; and, displaying the integrated products as a vertical profile of total mass flux of pollutant through the arcuate detection plane. As the wind changes, the downwind index point and arcuate pollution detection plane are redefined, so that the pollution sensor may be advanced peripherally with respect to the pollution source and driven through the arcuate detection plane for sensing.

DESCRIPTION OF THE PREFERRED EMBODIMENTS

Figure 1:
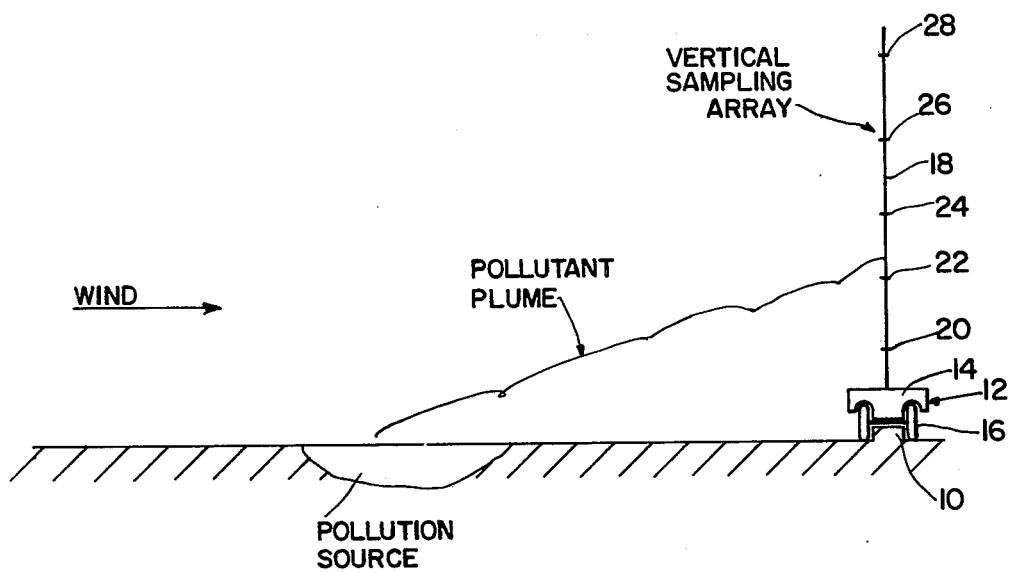
FIG. 1 is a fragmentary vertical elevation of a pollution source, such as an ore mine, showing a pollutant sensor vehicle with vertical antenna, being advanced in a peripheral arc with respect to the pollution source.
Figure 2:
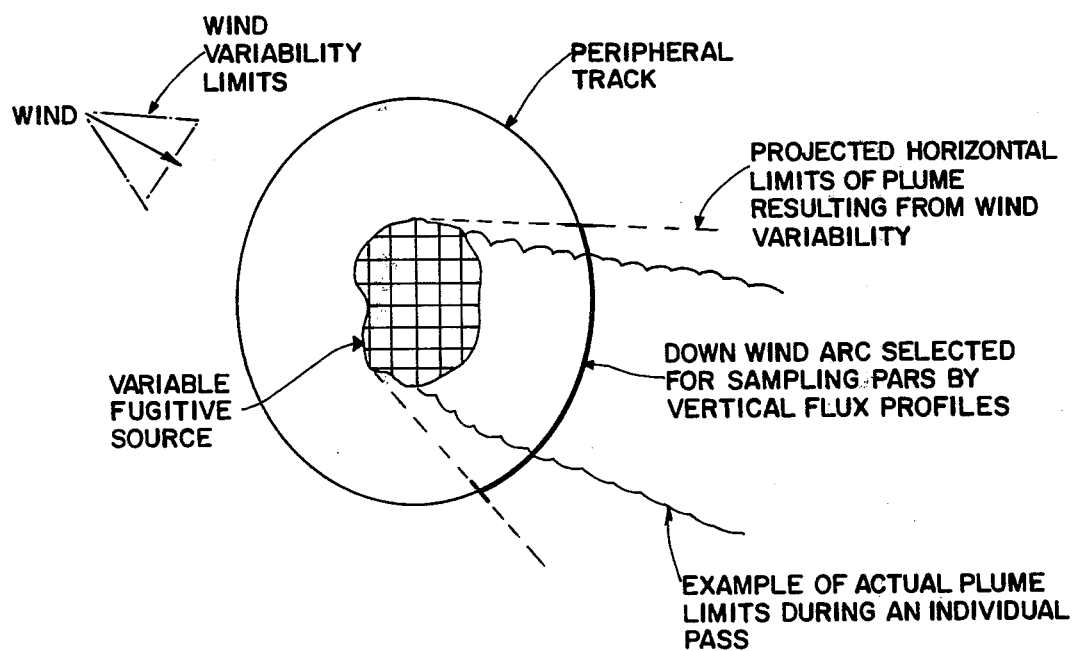
FIG. 2 is a top plan, showing the peripheral track for the pollutant sensor and definition of an arcuate pollution detection plane downwind of the pollution source.
Figure 3:
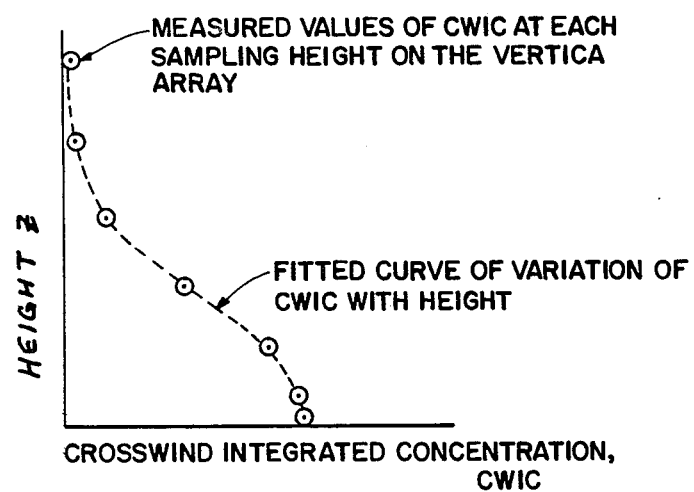
FIG. 3 is a graph showing crosswind integrated concentration, correlated with height of sensing within the arcuate detection plane.

The parent patent was oriented primarily toward pollution flux rate determination on an ad hoc or special study basis. Consequently, reference was made only to the conduct of cross-wind passes with a vertical array of instrumentation at an index point some distance downwind from the pollution source. It was presumed, therefore, that for a specific emission rate determination, the array and its associated vehicle would be employed necessarily on the downwind side.

The purpose of the present invention is to extend the application of the index point passes to the continuous or semicontinuous monitoring of emission rates under all wind direction which will occur over an extended period of time. For example, in a particular case for which the present invention is now being implemented, it is desired to monitor the amount of gaseous radon emanating from an open pit mine of high grate uranium over the lifetime of the mine, which may approach ten years. During the course of the mining, various portions and amounts of the ore body will be stripped of overburden, thereby enabling the free release of radon from the exposed surface. Since the source geometry and source intensity will be variable in time, it is required that a continuous monitoring system be employed.

According to this invention, the monitoring will be accomplished by defining a peripheral track which circumscribes the pollution source area. The peripheral track may consist of a narrow gauge railroad track, a pylon-suspended monorail, a pylon-supported suspension cable, or simply a graded pathway. Meteorological data will be continuously fed into a computer, where the wind direction and its variability will be assessed and an appropriate length of arc along the track will be defined as an arcuate detection plane by the computer, so as to insure that the downwind plume will be contained therein. The vehicle carrying the vertical instrumentation array (such as illustrated in FIG. 5 of the parent U.S. Pat. No. 4,135,092) may consist of a railway-mounted, monorail-mounted, or cable-mounted car, according to the track system employed; or a manned vehicle in case of the graded roadway; or an unmanned vehicle on the graded roadway with magnetic or radio frequency sensing of buried guidance cables or discretely spaced guidance check points, so as to maintain the vehicle on the roadway.

After determining the appropriate arc which will include the downwind plume, the computer will transmit instructions to either the automated or manned vehicle and the appropriate crosswind pass will be made along the arc. The fact that the pass is made along a crosswind arc, rather than a crosswind straight line introduces some error into the measurement of crosswind integrated concentration, but analysis shows that the error to be anticipated is only in the order of 4%.

By continuous monitoring of wind direction and its fluctuation, continuous updating of determination of the appropriate arc may be made, and corresponding successive passes accomplished by the vehicle and its vertical array. Each pass results in the measurement of a vertical series of crosswind integrated concentrations which are telemetered to the computer and, in turn, are integrated according to the methods described in the parent patent, so as to make an independent determination of the pollution source emission rate and its vertical distribution.

By successive application of the above sequence of operations, it is thus possible to maintain constant monitoring of the variations in source strength, regardless of wind direction, either immediately in sequence or at predetermined time intervals appropriate to the nature of the source and the operational requirements for information.

In FIG. 1 the pollution source is illustrated as emitting a pollutant plume, which is carried downwind. A pollution detection vehicle 12 is illustrated as including a carriage 14 and, wheel assembly 16, engaging track 10, which encompasses the pollution source in a peripheral arc. The pollution sensor vehicle 12 may include a vertical antenna 18, supporting a plurality of pollutant sensors, 20, 22, 24 and 26. One or more wind speed and direction sensors or anemometers 28 may be positioned upon the mast or adjacent thereto.

The measurement of crosswind integrated concentration by means of crosswind traverses of the pollutant sensors through the peripheral arc is accomplished by any one of the methods described in the parent patent. Conventional pollutant sensors or collectors may be employed. Also, of course, a vacuum pump may be mounted upon vehicle 12 for aspirating sample collectors.

Also, as in the parent patent, long wave infra-red absorption devices may be mounted upon the mast and a pair of vehicles 12, one supporting infra-red radiation transmitters upon its antenna and the other supporting a series of infra-red receptors upon its antenna, collimated with respect to the transmitters, may be driven through the peripheral arc.

In all cases, a wind recording system is employed in the vicinity of the vehicle 12, so as to obtain a vertical profile of wind speed and direction over the range of height being sampled and during the time interval of sampling. As in the parent patent, repeated crosswind passes with the various vertical arrays of sampling instruments will provide estimates of the median emission rate and its variation. As the wind changes, the index point and its concomittant arcuate pollution detection plane is redefined and the pollution sensors are repositioned along track 10, so as to be driven through the arcuate pollution detection plane on a continuous basis.

Manifestly, various types of pollutant sensors and supporting vehicles may be employed without departing from the spirit of the invention.

I claim:

1. Cylindrical method of quantifying fugitive emission rates from pollution sources comprising:
    A. driving a pollutant sensor in a peripheral arc surrounding a pollution source;
    B. gauging wind velocity and direction at an index point downwind of the pollution source;
    C. advancing said pollutant sensor to said index point;
    D. outlining at said index point an arcuate pollution detection plane, said plane being oriented transversely and vertically with respect to the wind;
    E. sensing pollutant concentration at a series of height intervals within the vertical and lateral confines of said arcuate pollution detection plane, so as to obtain integrated products of cross wind concentration and wind speed; and
    F. displaying said products as a vertical profile of total mass flux of pollutant through said detection plane.

2. Cylindrical method of quantifying fugitive emission rates into the atmosphere from pollution sources as in claim 1, wherein said outlining includes driving said pollutant sensor through a downwind segment of said peripheral arc, encompassing said index point.

3. Cylindrical method of quantifying fugitive emission rates into the atmosphere from pollution sources as in claim 1, wherein said outlining includes reciprocating said pollutant sensor within a downwind segment of said peripheral arc, encompassing said index point.

4. Cylindrical method of quantifying fugitive emission rates into the atmosphere from pollution sources as in claim 3, wherein said outlining of said pollutant detection plane is such that the vertical and lateral dimensions of said plane encompass a substantial portion of pollutant flux emanating from said pollution source.

5. Cylindrical method of quantifying fugitive emission rates into the atmosphere from pollution sources as in claim 2, wherein said outlining is such that the vertical and lateral dimensions of said arcuate pollution detection plane coincide with said vertical profile of pollutant flux.

6. Cylindrical method of quantifying figitive emission rates into the atmosphere from pollution sources as in claim 2, wherein said index point is sufficiently close to said pollution source such that said vertical profile of pollutant flux in said pollution detection plane is similar to the vertical profile of pollutant flux at said pollution source.

7. Cylindrical method of quantifying fugitive emission rates into the atmosphere from pollution sources as in claim 1, wherein said gauging of wind is at vertically spaced points within said arcuate pollution detection plane and is aligned with the axis thereof.

8. Cylindrical method of quantifying fugitive emission rates into the atmosphere from pollution sources as in claim 7, wherein said sensing of pollutant concentration at a series of height intervals is accomplished simultaneously at spaced vertical points within said pollution detection plane.

9. Cylindrical method of quantifying fugitive emission rates into the atmosphere from pollution sources as in claim 8, wherein said sensing within the lateral and vertical confines of said plane is accomplished sequentially crosswind within said pollution detection plane.

10. Cylindrical method of quantifying fugitive emission rates into the atmosphere from pollution sources as in claim 9, wherein said sensing is by lifting while moving sensing devices within the lateral and vertical confines of said pollution detection plane.

11. Cylindrical method of quantifying fugitive emission rates into the atmosphere from pollution sources as in claim 8, including infra-red sensing of said fugitive emissions.

12. Cylindrical method of quantifying fugitive emission rates into the atmosphere from pollution sources as in claim 9, wherein said infra-red sensing is correlated with elapsed time, as a measure of variation in fugitive emission intensity.

13. Cylindrical method of quantifying fugitive emission rates into the atmosphere from pollution sources as in claim 10, wherein said infra-red sensing is correlated with both elasped time and wind speed, as a measure of fugitive emission intensity.

14. Cylindrical method of quantifying fugitive emission rates into the atmosphere from pollution sources as in claim 7, including comparing downwind quantifying with similar upwind quantifying so as to relate incoming pollution with apparent fugitive emission rates.

15. Cylindrical method of quantifying fugitive emission rates into the atmosphere from pollution sources as in claim 7, wherein said sensing of pollutant concentration is accomplished sequentially at spaced vertical points within said pollution detection plane.

16. Cylindrical method of quantifying fugitive emission rates into the atmosphere from pollution sources as in claim 3, wherein said traversing is at a speed such that the concentration of pollutant is approximately constant.

17. Cylindrical method of quantifying fugitive emission rates into the atmosphere from pollution sources as in claim 3, including re-orienting said pollution detection plane, according to changes in wind direction.

18. Cylindrical method of quantifying fugitive emission rates into the atmosphere from pollution sources as in claim 3, including advancing said pollutant sensor throughout said peripheral arc, to a plurality of downwind index points, according to wind changes, and displaying said integrated products of crosswind concentration and wind speed as a factor of total fugitive emission from said pollution source.

* * * * *